United States Patent
Heinonen

[11] Patent Number: 6,131,572
[45] Date of Patent: Oct. 17, 2000

[54] MEDICAL DOSING DEVICE HAVING DOSING CHAMBER WITH A PRESSURE SENSOR

[75] Inventor: Erkki Heinonen, Helsinki, Finland

[73] Assignee: Instrumentarium Oy, Helsinki, Finland

[21] Appl. No.: 09/082,110

[22] Filed: May 20, 1998

[51] Int. Cl.[7] .................................................. A62B 9/02
[52] U.S. Cl. ........................... 128/205.24; 128/204.22
[58] Field of Search ..................... 128/205.24, 204.18, 128/204.22, 204.23, 204.26, 203.12, 205.23, 205.11, 204.21

[56] References Cited

U.S. PATENT DOCUMENTS

| | | |
|---|---|---|
| 4,023,587 | 5/1977 | Dobritz . |
| 5,005,570 | 4/1991 | Perkins ............................... 128/204.23 |
| 5,129,390 | 7/1992 | Chopin et al. . |
| 5,237,990 | 8/1993 | Psaros ............................... 128/204.21 |
| 5,299,568 | 4/1994 | Forare et al. . |
| 5,423,313 | 6/1995 | Olsson et al. ..................... 128/204.211 |
| 5,603,315 | 2/1997 | Sasso, Jr. ........................... 128/204.18 |
| 5,692,497 | 12/1997 | Schnitzer et al. ................. 128/204.21 |
| 5,931,160 | 8/1999 | Gilmore et al. ................... 128/204.21 |
| 5,937,853 | 8/1999 | Strom ................................ 128/204.23 |

FOREIGN PATENT DOCUMENTS

| | | | |
|---|---|---|---|
| 0 548 624 A1 | 12/1992 | European Pat. Off. .......... | 128/205.24 |
| 589751 | 3/1994 | European Pat. Off. . | |
| 659445 | 6/1995 | European Pat. Off. . | |
| 660091 | 6/1995 | European Pat. Off. . | |
| 806216 | 11/1997 | European Pat. Off. . | |
| 91/19526 | 12/1991 | WIPO ............................... | 128/205.19 |
| 92/11052 | 7/1992 | WIPO ............................... | 128/204.18 |

*Primary Examiner*—Aaron J. Lewis
*Assistant Examiner*—Teena Mitchell
*Attorney, Agent, or Firm*—Andrus, Sceales, Starke & Sawall

[57] ABSTRACT

A medical dosing device/method for providing small discrete volumes of gas, for example sulfur hexa fluoride or nitric oxide, to the breathing gases of a patient. The device includes a charging valve interposed between a gas supply and a dosing chamber. A discharge valve is connected between the dosing chamber and an outlet of the device. The dosing chamber has a pressure sensor connected to a control means for the valves. In operation, the control means closes the discharge valve and opens the charging valve until a predetermined pressure is sensed in the dosing chamber. The charging valve is closed and thereafter the discharge valve is opened to supply gas from the dosing chamber until the pressure sensed by the pressure sensor falls to a second, lower level. The discharge valve is then closed. The gas so discharged forms the volume of gas.

21 Claims, 2 Drawing Sheets

MEDICAL DOSING DEVICE HAVING DOSING CHAMBER WITH A PRESSURE SENSOR

BACKGROUND OF THE INVENTION

The present invention relates to a dosing device and method for dosing gas in discrete volumes from a pressurized gas supply. The device/method is designed to make the dosing precise, repeatable, and safe. The dosing device/method may be utilized in the delivery of e.g. sulphur hexa fluoride ($SF_6$) to the lungs of a patient for determining lung functional residual volume (FRC) or can be utilized with other gases for other diagnostic purposes. The device/method can also be used in inhaled nitric oxide (INO) therapy.

The gases dosed by the present invention are supplied in synchronism with the inspiration of the patient. State of the art dosing devices are based generally on gas flow measurement and control. See European patent publication 659,445 and U.S. patent application Ser. No. 5,918,596, filed Jul. 6, 1999 by the present inventor. However, these flow control systems tend to be expensive to manufacture due to the cost of flow sensors and the applicable control devices.

An alternative method is presented in European patent publication 806,216. This publication describes a constant volume dosing device comprising a charging valve, a dosing chamber, and a discharge valve. The charging valve is used to pressurize the dosing chamber with the constant pressure of the pressurized gas source. The discharge valve is used to relieve the pressure from the dosing chamber. Two different operational modes are suggested. In a first mode, the discharge valve is kept closed when the charging valve is opened to charge the chamber and then the reverse operation occurs. In a second mode, the charging valve is kept continuously open while the discharge valve is pulsed.

The device, however, does not fulfill existing safety requirements, especially when delivering gases, such as NO, which while therapeutic in proper doses are toxic in higher amounts. And, interruption of gas delivery may have immediate and disastrous effects on the patient. No means are presented by which one can determine the correct operation of the valves. This may lead to hidden failure of one or both valves and to severe overdosing of the patient. Or, if either of the valves is unable to open, underdosing without any notice will occur.

Another safety concern may arise when the dosing device is attached into the patient airway tube used to administer breathing gases to the patient, as shown in the European patent publication. The dosing device is supplied with high pressure from a source of dosing gas through a high pressure supply line. If a disconnection failure occurs in this high pressure supply line, an uncontrolled exhaust of gas can occur near the patient. The hazardousness of such an exhaust depends on the properties of the gas being administered. This hazard may be exacerbated by the fact that the high pressure supply line and the dosing device, when attached to the airway tube, are typically located in the most crowded working area of an intensive care unit. In addition to the high pressure supply line, also electrical signal lines to operate the valves have to be located in this crowded working environment. These multiple connections may reduce the ergonomics of the dosing system described in the '216 European patent publication.

BRIEF SUMMARY OF THE INVENTION

The present invention comprises a dosing chamber, a charging valve between the high pressure supply and an inlet of a dosing chamber, and a discharge valve connected to an outlet of the dosing chamber. The dosing chamber is equipped with one or more pressure sensors.

The charging valve is used to charge the dosing chamber with gas up to a pressure determined in accordance with a discrete dose volume. The charging of the chamber is monitored by the pressure sensor coupled to the dosing chamber. During charging, the discharge valve is kept closed. The discharge valve is opened to discharge gas from the dosing chamber until the pressure drops to a pressure also determined from the discrete dose volume. The discharge valve is then closed. The discharging is also monitored by the pressure sensor.

The pressure sensing carried out by the pressure sensor makes it possible to accurately deliver discrete dose volumes from the device of the invention without totally discharging the chamber. This advantageously results in diminished discharge time and diminished risk of contamination of the dosing device, since the pressure used for dosing can be kept continuously higher than the pressure existing in the breathing airway of the patient to which the doses are provided.

The dosing device of the present invention is able to vary the charging pressure of the dosing chamber. Inasmuch as the discharge flow is a function of the discharge pressure, this ability allows the discharge flow to be controlled. This extends the dynamic control range of the delivery system compared to a fixed charging pressure type device operating with a fixed charging pressure.

The pressure monitoring carried out by the pressure sensor makes it also possible to evaluate the operative status of the charging and discharge valves. If either of the valves becomes jammed closed, the measured pressure will not correspond to that found when the valves are operating properly. If either of the valves leak, monitoring of the chamber pressure will ascertain pressure changes indicative of such leaks. Redundancy for the pressure sensor will further add to safety in critical applications.

Supplying the gas pulse doses to be administered through a carrier gas delivery system according to the aforesaid U.S. patent application Ser. No. 08/841,466 significantly improves the safety and ergonomics of the working environment inasmuch as no high pressure gas supply line or electrical control lines are needed in the crowded area around the patient. The only additions into this area required are the small carrier gas line to breathing circuit for the patient and a connection for same. A further advantage arising from the usage of the carrier gas delivery system of the present invention is the avoidance of contamination of the dosing device since the device is located far from the contaminated areas of the breathing circuit.

BRIEF DESCRIPTION OF THE SEVERAL VIEWS OF THE DRAWING

Additional features and advantages of the present invention will become apparent from the following detailed description of the present invention taken in conjunction with the accompanying drawing in which.

DETAILED DESCRIPTION OF THE INVENTION

Figure 1:
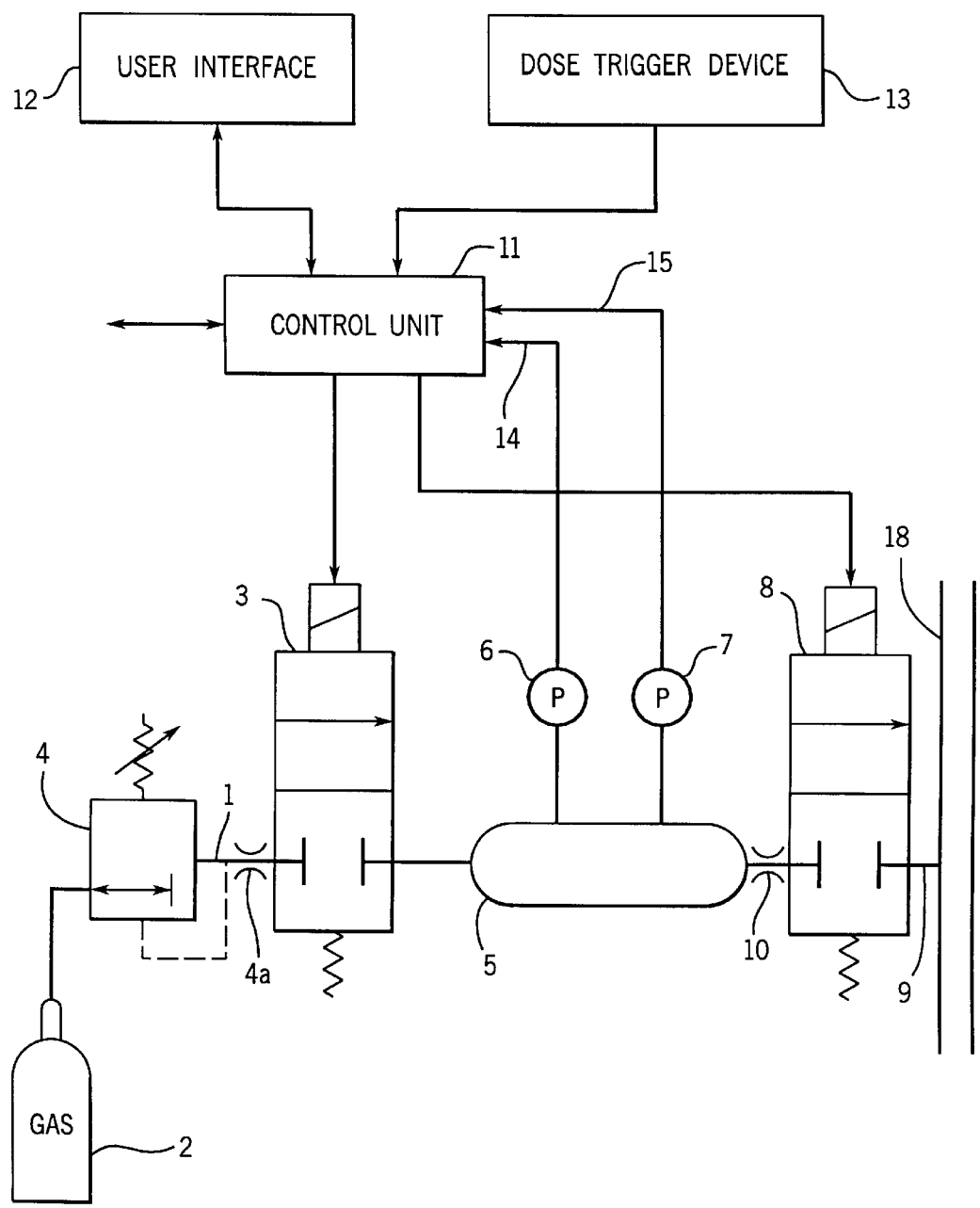
FIG. 1 is a diagram showing the dosing device of the present invention.

As shown in FIG. 1, gas supply line 1 is connected between a high pressure source 2 of dosing gas and the inlet of the dosing device of the present invention. Optionally, one or more pressure regulators 4 may be inserted in this supply line for setting the supply pressure at an optimal level for the dosing device.

The dosing device has charging valve 3 connected to the dosing device inlet. Charging valve 3 can be either of a proportional or a digital type. In a proportional valve, the degree of opening is proportional to the magnitude of a voltage or current input signal to an electrical actuator for the valve. The quality of proportionality is determined by the electrical and mechanical characteristics of the valve and actuator. The operation of a digital valve is such that it is either fully open or fully closed. When using a digital valve as charging valve 3 there may be uncontrollability of the charging if the charging flow is large and the volume of dosing chamber 5 connected to the valve is small. This problem can be remedied by use of a flow restrictor, such as 4a, in supply line 1 preferably at the inlet of charging valve 3.

The outlet of charging valve 3 is connected to the inlet of dosing chamber 5. Dosing chamber 5 is provided with pressure sensors 6 and 7. Two sensors add safety, such as improved failure recognition, to the operation of the dosing device, but satisfactory operation can be achieved with a single sensor, as well. Pressure sensor(s) 6, 7 may be of any suitable type.

Discharge valve 8 is connected to the outlet of dosing chamber 5. Discharge valve 8 releases the charged pressure from dosing chamber 5 to the outlet of the dosing device and into the dosing line 9 to the patient. Discharge valve 8 can also be either of the proportional or digital type. It is to be recognized that a digital valve may be imprecise in delivering very small volumes due to the high discharge flow through the valve. To ensure desirable delivery properties, a fixed flow restrictor 10 may be inserted between dosing chamber 5 and discharge valve 8 to optimize the discharge flow for the particular dosing chamber volume and required dosing time.

Charging valve 3, pressure sensors 6, 7, and discharge valve 8 are connected to control unit 11. This control unit is further connected to a user interface 12 for receiving the required operation data, such as dose volume and dose timing information. User interface 12 also displays the operational and status information with respect to the delivery of the gas doses. This information may include alarms, delivered dose volumes, and dosing chamber pressure. Control unit 11 is also connected to dose triggering device 13 for supplying the control unit with triggering information for synchronizing the gas dosing with the breathing pattern of the patient according to information received from user interface 12 or, alternatively, preset default triggering information.

Pressure sensors 6, 7 serve multiple purposes in the dosing device of the present invention. The signals to control unit 11 provided through signal lines 14 and 15 can be compared between each other to deduce the operative status of the sensors. The pressure sensors can be used also to assure the proper operation of the pressurized gas supply, and of the charging and discharge valves, 3, 8. Keeping discharge valve 8 closed and opening charging valve 3 should raise the pressure in dosing chamber 5, assuming the presence of the pressure supply and the proper function of charging valve 3. After closing charging valve 3, the dosing chamber pressure should remain constant as long discharge valve 8 is closed, unless there is a leakage either in the discharge valve or elsewhere within the dosing chamber.

Opening discharge valve 8 should result in rapid discharge of the chamber pressure. If not, there is a discharge valve control problem present. If there is leakage through charging valve 3, closing discharge valve 8 will result in continuous pressure increase within dosing chamber 5. This can be detected by pressure sensors 6, 7.

To supply a dose of gas, charging valve 3 is opened to charge dosing chamber 5 with gas up to a pressure determined in accordance with a desired, discrete dose volume. Discharge valve 8 is closed. The charging of dosing chamber 5 is monitored by pressure sensor 6, 7. When the pressure in dosing chamber 5 reaches a first predetermined pressure, charging valve 3 is closed. At the time of dose delivery, discharge valve 8 is opened to supply gas from dosing chamber 5 to the outlet of the dosing device until the pressure in the dosing device has dropped to a second, lower, predetermined pressure. The gas so supplied forms the discrete volume of gas.

Typical doses of sulphur hexa fluoride used for determining lung functional residual volume (FRC) vary from 0.5 ml to 10 ml depending on the amount of ventilation and on lung volume. A typical adult dose could be 3 ml.

Pressure sensor 6, 7, make it possible to accurately deliver the desired gas volume without totally discharging dosing chamber 5. The residual pressure in dosing chamber 5 can be kept higher than the pressure in the patient's breathing airway, thereby lessening or avoiding the risk of contaminating the dosing device.

The dosage control cycle is based on the dosing chamber pressure measured by sensors 6, 7. The charging pressure is selected to charge enough gas into dosing chamber 5 for a sufficient dose volume for the next discharge. The charging pressure is calculated from the equation $$P_{charge} = \left(\frac{V_{dose}}{V_{chamber}} \times P_{amb}\right) + P_{discharge}$$

where $P_{charge}$=the absolute pressure to which the chamber is to be charged $V_{dose}$=the required dose volume $V_{chamber}$=dosing chamber volume $P_{amb}$=absolute ambient pressure $P_{discharge} > P_{amb}$, and is the absolute pressure to which the chamber is to be discharged in delivering the dose.

Thus, the dose volume is $$V_{dose} = \left(\frac{P_{charge} - P_{discharge}}{P_{amb}}\right) \times V_{chamber}$$

Due to inaccuracies, for example, in the timing of the charging and discharge valve control, the pressures $P_{charge}$ and $P_{discharging}$ will most likely not be completely reached during the course of a dose delivery. The actual delivered dose will be determined from the chamber pressure prior to opening the discharge valve and the chamber pressure after closing the discharge valve, but before recharging the chamber. The true volume of the delivered dose is $$V = \left(\frac{P_{before} - P_{after}}{P_{amb}}\right) \times V_{chamber}$$

Figure 2:
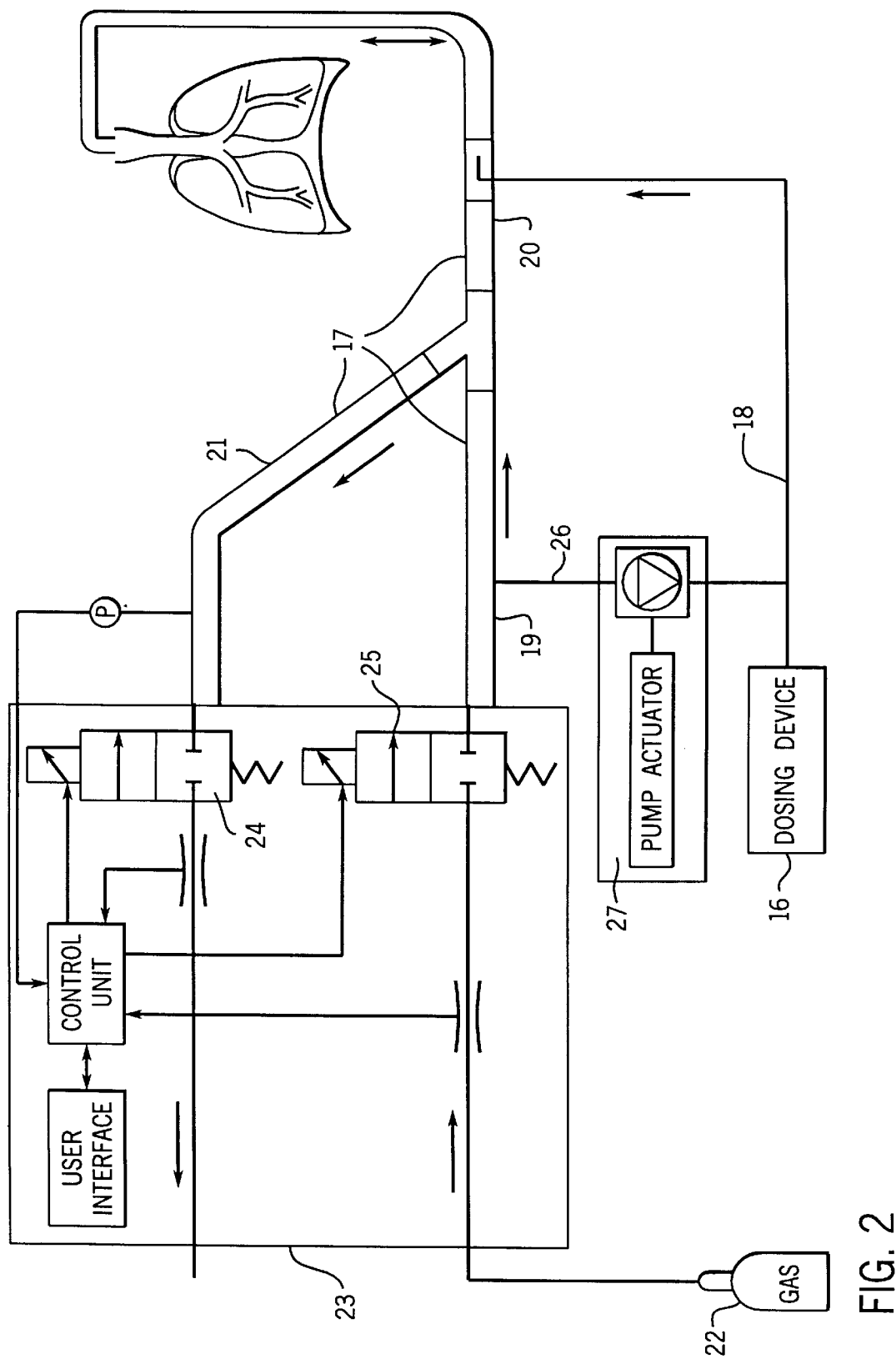
FIG. 2 shows the dosing device in conjunction with a carrier gas supply system and a patient breathing circuit and ventilation system.

The connection of a dosing device 16 of the present invention into patient breathing circuit 17 through a carrier gas line 18 is shown in FIG. 2. Breathing circuit 17 comprises inspiratory limb 19, patient limb 20, and expiratory limb 21. Inspiratory gas is delivered from gas supply 22 through a ventilator 23 to inspiratory limb 19 to be delivered to the patient during inhalation. The ventilator provides inhalation gas flow by closing the expiratory valve 24 and opening one or more inspiratory valves 25 so that gas flows from gas supply 22 to the patient. The inspiration is stopped by closing the inspiratory valve(s). Exhalation is started by opening expiration valve 24. Dose trigger information to the dosing device 16 of the present invention, such as that described in connection with element 13 of FIG. 1, can be provided by ventilator 23, or alternatively the breathing circuit may be equipped with appropriate flow or pressure sensing systems (not shown).

The dose of gas is advantageously delivered at the beginning of each inspiration. However, it may be delivered at other times in the respiratory cycle or one or more respiratory cycles may be skipped. Also, each dose of gas may have the same volume or successive doses of gas may vary in volume.

Dosing device 16 delivers the gas doses into carrier gas line 18. This carrier gas line starts from carrier gas flow generator 27 which in the most simplified form is a pump. The carrier gas flow generator creates a high speed gas flow in the carrier gas line to prevent any dosed gas from being trapped in the carrier gas line at the end of dosing. The carrier gas flow generator may have a suction line 26 connection to the inspiratory limb 19 of the breathing circuit for suctioning the gas from the circuit for use as the carrier gas so that the composition of the breathing gas is not affected. The downstream end of carrier gas line 18 discharges the gas flow in the line into patient limb 20 or into the upper airways of the patient.

Proper communication between the discharge end of the carrier gas line and breathing circuit 17 is an important requirement for successful delivery of the gas doses through carrier gas line 18. This communication can be assured through the use of pressure sensors 6, 7 of dosing device 16 by loading dosing chamber 5 to a pressure such that it will be totally discharged in the next dose. After a dose is delivered, carrier gas flow is stopped and discharge valve 8 is left open. The pressure within dosing chamber 5 will then balance with the pressure in carrier gas line 18, which equals the pressure at the discharge end of carrier gas line 18 in the breathing circuit 17. If this pressure is constant, disconnection of the carrier gas line and a loss of communication is likely, since with the line connected, pressure sensors 6, 7 will reflect the varying pressure of the breathing circuit. If the discharge point is located at the distal end of an endotracheal tube in the patient's airway, the foregoing procedure gives an opportunity also for intrathoracic pressure measurement.

It is recognized that other equivalents, alternatives, and modifications aside from those expressly stated, are possible and within the scope of the appended claims.

I claim:

1. A medical dosing device for providing a discrete volume of gas from a pressurized gas supply, said dosing device comprising:

a control means;

an inlet connectable to the pressurized gas supply;

an outlet supplying the volume of gas;

a dosing chamber interposed between said inlet of said dosing device and said outlet of said dosing device, said dosing chamber having an inlet and an outlet;

a charging valve coupled to said inlet of said dosing device and to said inlet of said dosing chamber, said charging valve being operable by said control means, said charging valve admitting gas from the pressurized gas supply to said dosing chamber when open and sealing the inlet of said dosing chamber when closed;

a discharge valve coupled to said outlet of said dosing chamber and to said outlet of said dosing device, said discharge valve being operable by said control means, said discharge valve sealing the outlet of said dosing chamber when closed and discharging gas from said dosing chamber to said outlet of said dosing device when open;

at least one pressure sensor coupled to said dosing chamber for detecting the pressure in said dosing chamber, said pressure sensor being couplable to the control means;

said dosing chamber being charged with gas to a first predetermined pressure which is sensed by said pressure sensor when said discharge valve is closed and said charging valve is open, said discharge valve being opened to supply gas from said dosing chamber to said outlet of said dosing device until the pressure in the dosing chamber drops to a second, lower, predetermined pressure, the gas so supplied forming a discrete volume of gas.

2. The dosing device according to claim 1 wherein at least one of said charging valve and discharge valve comprises a proportional valve.

3. The dosing device according to claim 1 wherein at least one of said charging valve and discharge valve comprises a digital valve.

4. The dosing device according to claim 3 further including a flow restrictor operatively associated with said digital valve.

5. The dosing device according to claim 1 including a pair of pressure sensors coupled to said dosing chamber.

6. The dosing device according to claim 1 wherein said dosing device further includes said control means coupled to said charging valve, discharge valve, and pressure sensor.

7. The dosing device according to claim 6 wherein said control means includes a user interface unit for inputting operational data relating to said dosing device.

8. The dosing device according to claim 7 wherein one of said control means and user interface unit includes means for displaying operational information regarding said dosing device.

9. The dosing device according to claim 6 wherein said control means includes dose triggering means for timing the operation of said dosing device.

10. The dosing device according to claim 6 further including a pair of pressure sensors and wherein said control means is further defined as a control means for comparing the pressure sensing obtained by said pair of pressure sensors and determining the operative condition of said pressure sensors from said comparison.

11. The dosing device according to claim 6 wherein said control means is further defined as a control means for closing said discharge valve, opening said charging valve to charge said dosing chamber with gas, closing the charging valve, and determining the pressure sensed by said pressure sensor over a period of time to ascertain the functioning of said valves.

12. The dosing device according to claim 11 wherein said control means is further defined as opening said discharge valve and sensing pressure conditions in said dosing chamber.

13. The dosing device according to claim 1 further comprising a patient ventilating device, said dosing device providing said discrete volume of gas to said patient ventilating device, which in turn provides said discrete volume of gas to a patient.

14. The apparatus according to claim 13 wherein the patient ventilating device includes means for providing a carrier gas flow conduit to the ventilating device and wherein said outlet of said dosing device is further defined as couplable to said carrier gas conduit for supplying the discrete volume of gas to carrier gas flowing in the carrier gas flow conduit.

15. A method for providing a discrete volume of gas from a pressurized gas supply for medical purposes, said method comprising the steps of:

provided a dosing chamber in communication with the pressurized gas supply;

charging the dosing chamber with gas from the gas supply;

providing a sensor for sensing the gas pressure in the dosing chamber;

sensing the gas pressure in the dosing chamber to determine when the gas pressure sensed in the dosing chamber reaches a first predetermined pressure;

terminating charging of the dosing chamber when the gas pressure in the dosing chamber reaches the first predetermined pressure;

providing a discharge valve at an outlet of the dosing chamber: and discharging gas from the dosing chamber until the pressure drops to a second, lower predetermined gas pressure, the gas so discharged forming essentially said discrete volume of gas.

16. The method according to claim 15 further defined as terminating charging of the dosing chamber when the gas pressure in the dosing chamber reaches a first predetermined pressure determined in accordance with the gas volume to be provided.

17. The dosing method according to claim 15 wherein the sensing of the gas pressure is carried out with a pair of pressure sensors and wherein the method is further defined as comparing the pressure sensed by the pair of pressure sensors and determining the operative condition of the pressure sensors from the comparison.

18. The dosing method according to claim 15 wherein the steps of charging and discharging the dosing chamber are carried out with controllable valves and wherein the method further includes the steps of charging the dosing chamber with gas from the gas supply and sealing the dosing chamber; and ascertaining pressure conditions in the sealed dosing chamber over a period of time to determine the condition of the valves.

19. The dosing method according to claim 18 further defined as including the step of discharging gas from the dosing chamber and sensing pressure conditions in the dosing chamber to determine the condition of the valves.

20. The dosing method according to claim 15 further defined as a method for providing a volume of gas to a patient ventilating device for providing a volume of gas to a patient.

21. The dosing method according to claim 20 further defined as a method for providing a volume of gas to a carrier gas for provision to the patient.

* * * * *